(12) United States Patent
Dickinson

(10) Patent No.: US 8,795,338 B2
(45) Date of Patent: Aug. 5, 2014

(54) ANTI-SPLAY MEMBER FOR BONE FASTENER

(75) Inventor: Charles Dickinson, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 251 days.

(21) Appl. No.: 13/273,308

(22) Filed: Oct. 14, 2011

(65) Prior Publication Data

US 2013/0096616 A1 Apr. 18, 2013

(51) Int. Cl.
*A61B 17/70* (2006.01)

(52) U.S. Cl.
CPC ......... *A61B 17/7032* (2013.01); *A61B 17/7037* (2013.01)
USPC .......................................... 606/273; 606/305

(58) Field of Classification Search
CPC ........... A61B 17/7001; A61B 17/7032; A61B 17/7037
USPC .................................................. 606/264–274
See application file for complete search history.

(56) References Cited

U.S. PATENT DOCUMENTS

| | | | |
|---|---|---|---|
| 6,077,262 A * | 6/2000 | Schlapfer et al. | 606/305 |
| 6,755,829 B1 * | 6/2004 | Bono et al. | 606/308 |
| 6,786,903 B2 * | 9/2004 | Lin | 606/23 |
| 7,294,128 B2 * | 11/2007 | Alleyne et al. | 606/279 |
| 7,476,239 B2 | 1/2009 | Jackson | |
| 7,503,924 B2 * | 3/2009 | Lee et al. | 606/272 |
| 7,513,905 B2 | 4/2009 | Jackson | |
| 7,572,279 B2 | 8/2009 | Jackson | |
| 7,695,497 B2 * | 4/2010 | Cordaro et al. | 606/267 |
| 7,776,067 B2 | 8/2010 | Jackson | |
| 7,789,896 B2 | 9/2010 | Jackson | |
| 8,016,862 B2 * | 9/2011 | Felix et al. | 606/270 |
| 8,034,086 B2 * | 10/2011 | Iott et al. | 606/267 |
| 8,465,528 B2 * | 6/2013 | Schumacher | 606/273 |
| 2004/0030337 A1 | 2/2004 | Alleyne | |
| 2004/0039383 A1 | 2/2004 | Jackson | |
| 2004/0059332 A1 | 3/2004 | Roussouly | |
| 2004/0147928 A1 | 7/2004 | Landry | |
| 2004/0167523 A1 | 8/2004 | Jackson | |
| 2004/0193157 A1 | 9/2004 | Falahee | |
| 2004/0260284 A1 | 12/2004 | Parker | |
| 2005/0277924 A1 | 12/2005 | Roychowdhury | |
| 2006/0025771 A1 | 2/2006 | Jackson | |
| 2006/0058794 A1 | 3/2006 | Jackson | |
| 2006/0064089 A1 | 3/2006 | Jackson | |
| 2006/0129149 A1 * | 6/2006 | Iott et al. | 606/61 |
| 2006/0293674 A1 | 12/2006 | Li | |
| 2006/0293675 A1 | 12/2006 | Li | |
| 2007/0083199 A1 | 4/2007 | Baccelli | |
| 2007/0233086 A1 | 10/2007 | Harms | |
| 2007/0233117 A1 | 10/2007 | Butler | |
| 2008/0004625 A1 | 1/2008 | Runco | |
| 2008/0039848 A1 | 2/2008 | Jackson | |
| 2008/0058811 A1 * | 3/2008 | Alleyne et al. | 606/61 |
| 2009/0082819 A1 * | 3/2009 | Blain et al. | 606/308 |

* cited by examiner

*Primary Examiner* — Ellen C Hammond

(57) ABSTRACT

An anti-splay member is configured for engagement with a bone fastener and includes a body defining a longitudinal axis and a threaded cavity extending along the longitudinal axis. The cavity is configured for engagement with a screw. Opposing retainer members extend transversely from the body and are configured to engage a proximal end of the bone fastener to prevent radial expansion of the proximal end. At least one locking member extends from the body and is configured for engagement with the proximal end of the bone fastener. Methods of use are disclosed.

19 Claims, 6 Drawing Sheets

ANTI-SPLAY MEMBER FOR BONE FASTENER

TECHNICAL FIELD

The present disclosure generally relates to medical devices, systems and methods for the treatment of musculoskeletal disorders, and more particularly to a spinal implant fixation system and method that employs bone fasteners to provide stabilization of vertebrae.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes discectomy, laminectomy, fusion and implantable prosthetics. During surgical treatment, one or more rods may be attached via fasteners to the exterior of two or more vertebral members. This disclosure describes an improvement over these prior art technologies.

SUMMARY

Accordingly, an anti-splay member configured for engagement with a bone fastener is provided, which comprises a body defining a longitudinal axis and a threaded cavity extending along the longitudinal axis. The cavity is configured for engagement with a screw. Opposing retainer members extend transversely from the body and are configured to engage a proximal end of the bone fastener to prevent radial expansion of the proximal end. At least one locking member extends from the body and is configured for engagement with the proximal end of the bone fastener.

In one embodiment, a bone fastener includes a proximal end including a receiver that defines an implant cavity. The proximal end further including a body defining a longitudinal axis and a threaded cavity extending along the longitudinal axis. The cavity being configured for engagement with a screw. Opposing retainer members extend transversely from the body and are configured to engage a proximal end of the bone fastener to prevent radial expansion of the proximal end. At least one locking member extending from the body and being configured for engagement with the proximal end of the bone fastener. The bone fastener further includes a distal end configured for penetrating tissue.

In one embodiment, a vertebral rod system includes a multi-axial bone fastener including a proximal end and a distal end. The proximal end of the bone fastener including a receiver having opposing walls that define a U-shaped channel. Each of the walls include an engagement platform defining proximal and transverse facing surfaces, and a transverse opening. An anti-splay member includes a body defining a longitudinal axis and a threaded cavity extending along the longitudinal axis. The cavity is configured for engagement with a screw. The body including opposing retainer members extending transversely from the body and being configured to engage the surfaces of the engagement platform to prevent radial expansion of the proximal end. The body further including at least one locking member extending from the body and being configured for engagement with the transverse opening. A vertebral rod is configured for disposal within the channel.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
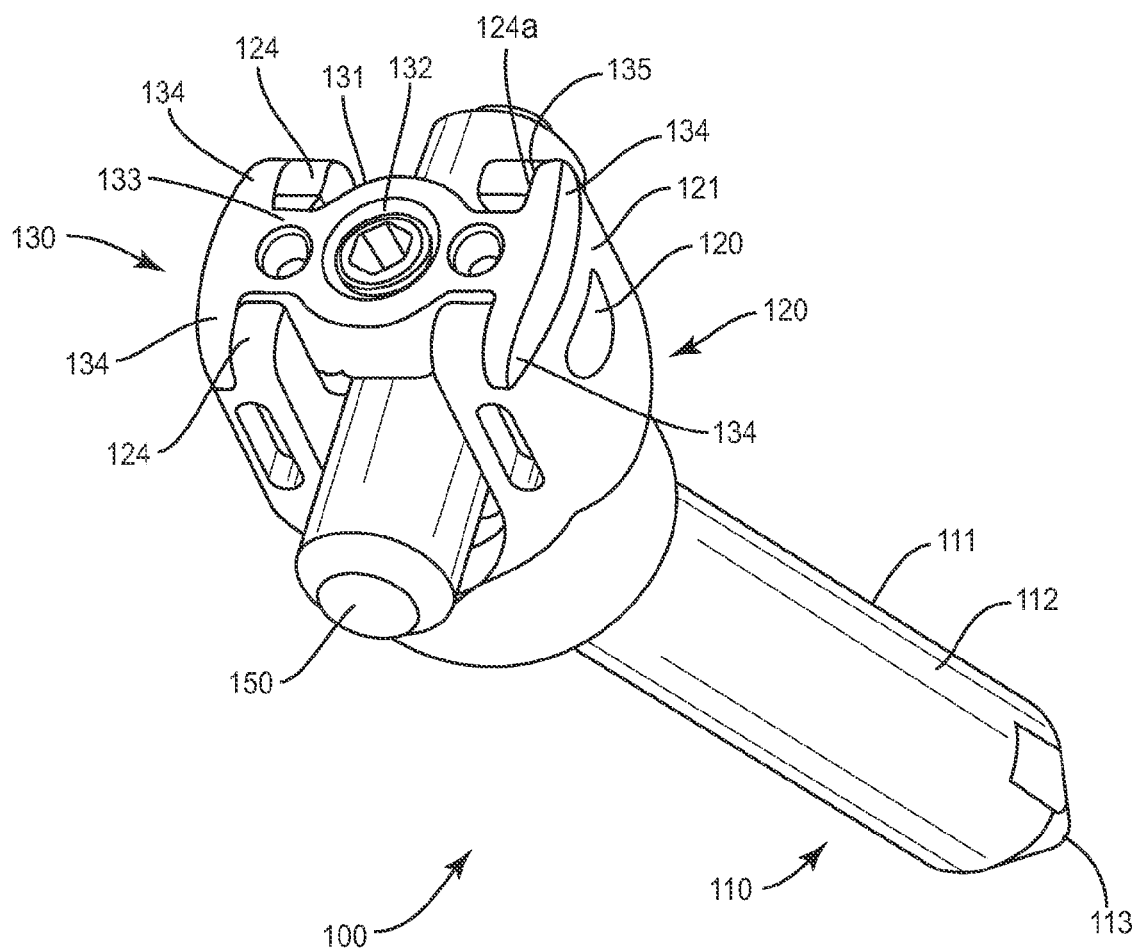
FIG. 1 is a perspective view of a multi-axial bone fastener system in accordance with the principles of the present disclosure.

The exemplary embodiments of bone fastener system and related methods of use disclosed are discussed in terms of medical devices for the treatment of musculoskeletal disorders and more particularly, in terms of a spinal implant fixation system and method that employs bone fasteners to provide stabilization of vertebrae.

In one embodiment, the bone fastener has an anti-splay member provided in an outer setscrew housing. It is envisioned that the outer setscrew housing has one or more flexible locking members, such as, for example, flexible ears, and two holes for an inserter instrument. It is further envisioned that an inner set screw can be inserted after the outer setscrew housing is mounted to the receiver, which may be pre-assembled before installing.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed bone fastener and system may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The present disclosure may also be alternatively employed with procedures for treating the lumbar, cervical, thoracic and pelvic regions of a spinal column. The bone fastener and system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of the system can be fabricated from biologically acceptable materials suitable for medical applications, including metals, synthetic polymers, ceramics and bone material and/or their composites, depending on the particular application and/or preference of a medical practitioner. For example, the components of the bone fastener and system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic conical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the system may have material composites, including the above materials, to achieve various desired characteristics such as strength, rigidity, elasticity, compliance, biomechanical performance, durability and radiolucency or imaging preference. The components of the system, individually or collectively, may also be fabricated from a heterogeneous material such as a combination of two or more of the above-described materials.

The following discussion includes a description of a system and related methods of employing the bone fastener and system in accordance with the principles of the present disclosure. Alternate embodiments are also disclosed. Reference will now be made in detail to the exemplary embodiments of the present disclosure, which are illustrated in the accompanying figures.

Turning now to FIGS. 1-7, there is illustrated components of a bone fastener and system in accordance with the principles of the present disclosure. Bone fastener 100 is employed with a system, such as, for example, a vertebral rod system, which is configured for attachment to bone, such as, for example, vertebrae V (as shown, for example, in FIGS. 6 and 7) during surgical treatment of a spinal disorder, examples of which are discussed herein. Referring to FIGS. 1 to 5, bone fastener 100 includes an elongated bone penetrating member 110 including a shank 111 having an outer surface 112 which is preferably threaded to allow bone penetrating member 110 to function as a bone screw. Shank 111 has a cylindrical shaft configuration. Proximal end 114 includes a rounded head configured to fit within an interior cavity of a base, as discussed below, while allowing rotation and articulation of the bone penetrating member.

Figure 6:
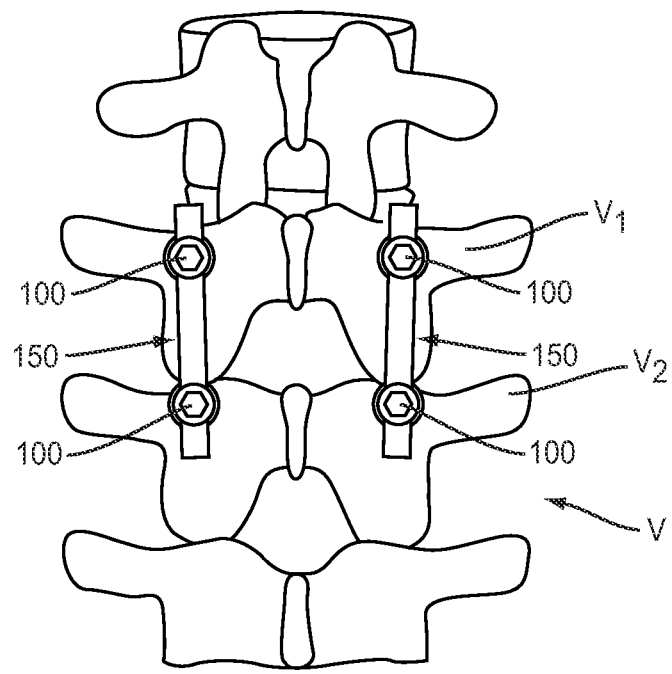
FIG. 6 is a front view of the bone fastener system shown in FIG. 1 with vertebrae.
Figure 7:
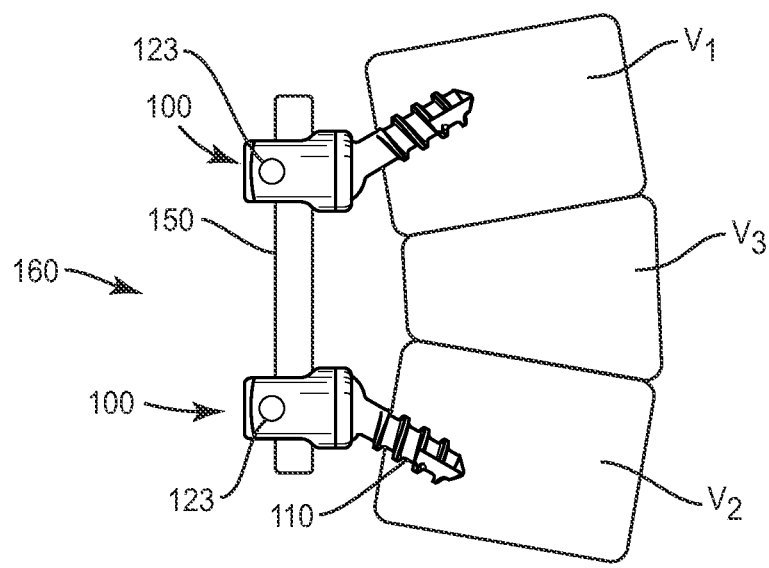
FIG. 7 is a side view of the bone fastener system and vertebrae shown in FIG. 6.

Shank 111 defines a longitudinal axis $L_1$ and is configured for fixation with vertebrae V (FIGS. 6 and 7). It is contemplated that bone penetrating member 110 may include alternate bone fixation elements, such as, for example, a nail configuration, barbs, and/or expanding elements.

It is contemplated that bone penetrating member 110 can be variously dimensioned, for example, with regard to length, width, diameter and thickness. It is further contemplated that the respective cross-sectional geometry of member 110 may have various configurations, for example, round, oval, rectangular, irregular, consistent, variable, uniform and non-uniform. Member 110 may have a different cross-sectional area, geometry, material or material property such as strength, modulus or flexibility relative to shank 111.

Bone fastener 100 further includes a receiver 120 for a vertebral rod 150. More particularly, receiver 120 includes a body 121 defining a longitudinal axis $L_2$ (FIG. 4) and having upright arms 122 which are spaced apart so as to define an implant cavity, such as, for example, a U-shaped channel 128 to receive a vertebral rod 150 in a lateral orientation. It is contemplated that the implant cavity may include various configurations, such as, for example, V-shaped, W-shaped, tapered, uniform, non-uniform, offset and/or staggered. It is further contemplated that arms 122 may be oriented relative to one another at various angular orientations, such as, for example, parallel, acute, obtuse, perpendicular, offset and/or staggered. Arms 122 possess lateral openings 123 at least partially defined by an upper ridge 123a (FIG. 3) which serves as abutment surface as described below. Receiver arms 122 each possess two upwardly projecting teeth 124 which are spaced apart so as to define a gap 126 between them (FIG. 4). It is contemplated that arms 122 may include one or a plurality of teeth 124. Teeth 124 each have a vertical outer surface 124a which intersects with a horizontal upward facing ledge 125. Receiver 120 includes an interior cavity 127 in which the proximal end 114 of the bone penetrating member is rotatably and articulatingly disposed. For example, the bone penetrating member 110 can rotate around axis $L_1$ and can also be positioned at an angle A in a range of approximately +/–30 degrees from axis $L_2$ with rotation around axis $L_2$.

An anti-splay member 130 engages the upright arms 122 to prevent splaying, or radially outward bending of the arms. The implanted bone fastener system accommodates the flexing of the spinal column and concomitant forces on the rod 150 which, in turn, exerts force against the inner surfaces of the upright arms 122. Anti-splay member 130 is configured to prevent the bias of the upright arms 122 from splaying radially outward. It is contemplated that splaying of the upright arms 122 may loosen the engagement between the rod 150 and the receiver 120, which may require subsequent surgical treatment, such as, for example, further adjustment and/or replacement of components of the system.

Figure 2:
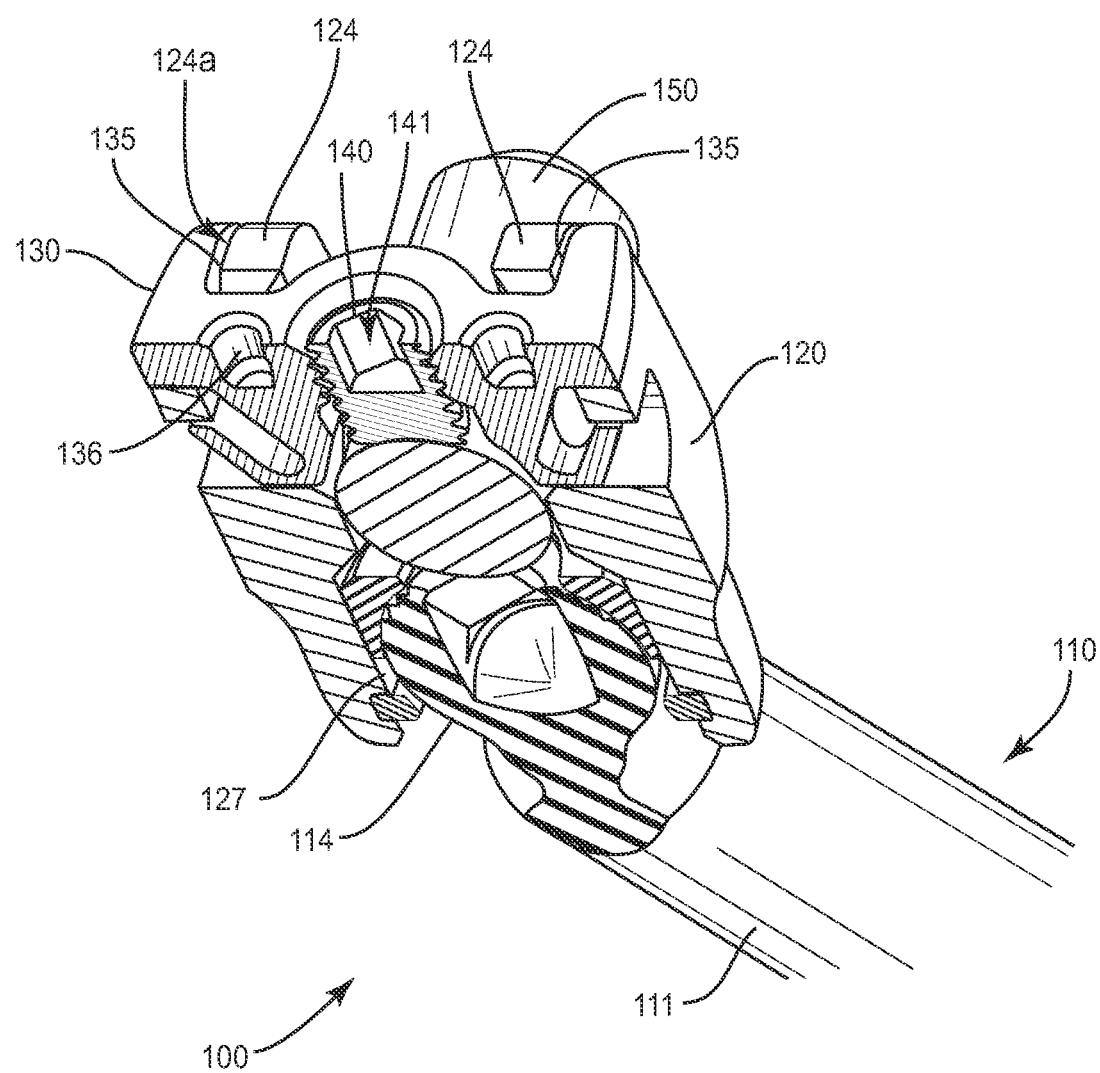
FIG. 2 is a partially cut away perspective view of the bone fastener system shown in FIG. 1.
Figure 3:
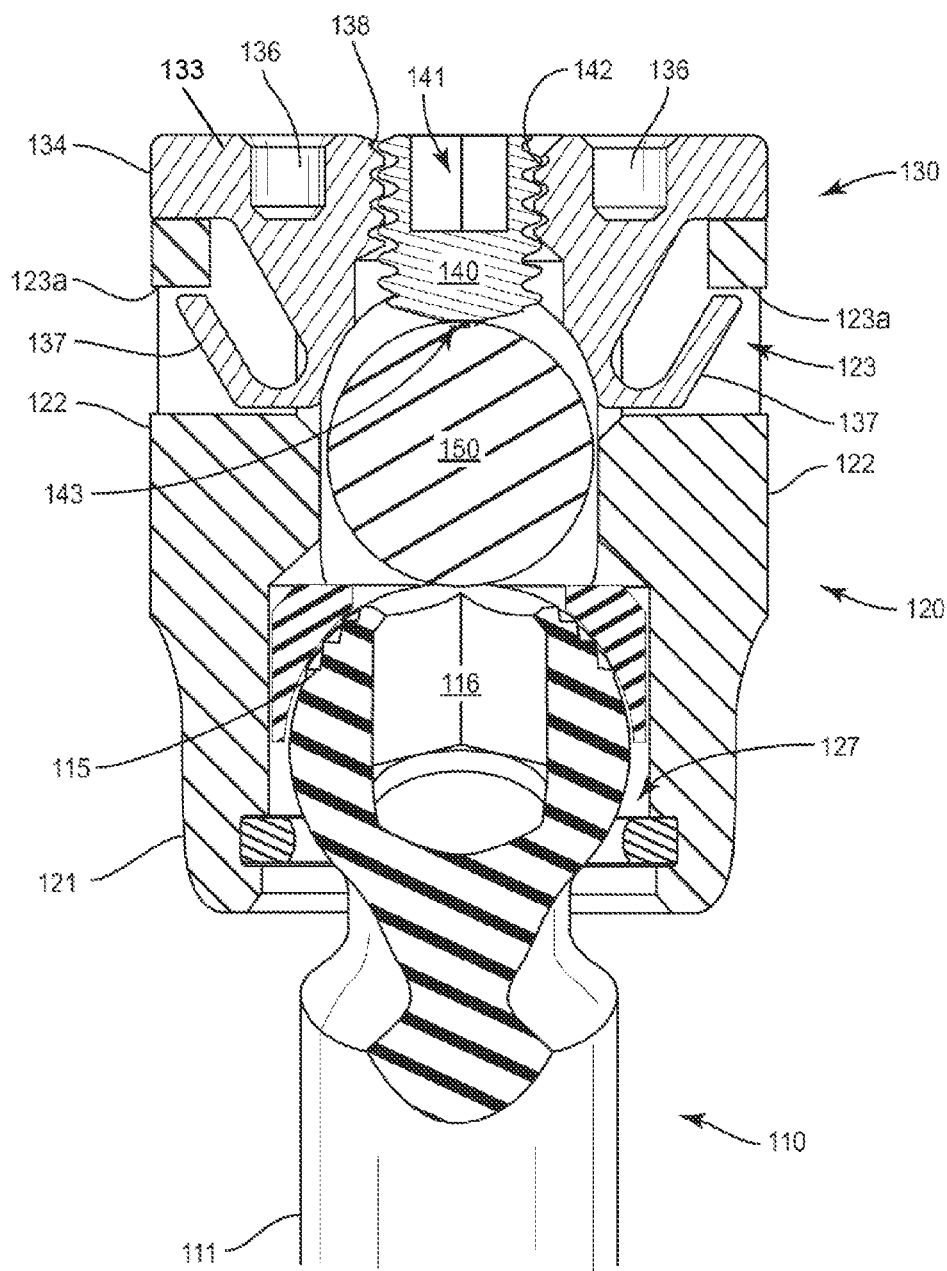
FIG. 3 is a side view, in part cross section, of the bone fastener system shown in FIG. 1.
Figure 4:
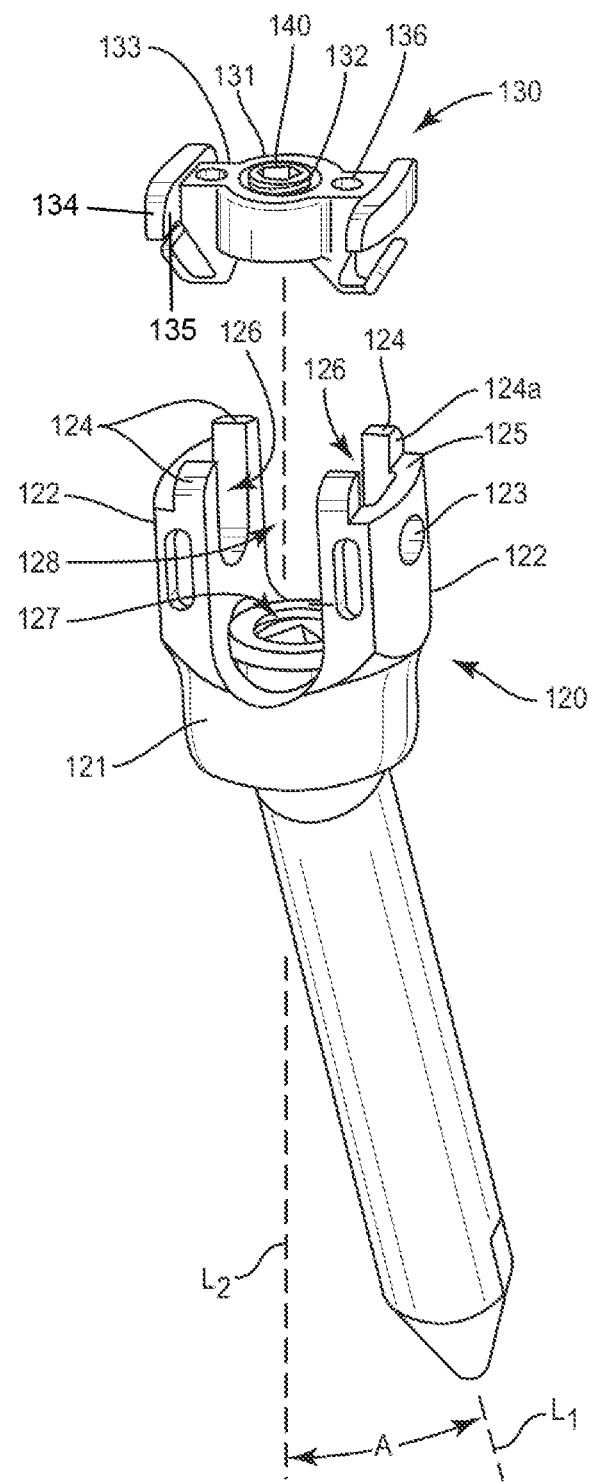
FIG. 4 is a perspective view of the bone fastener system shown in FIG. 1 with parts separated.
Figure 5:
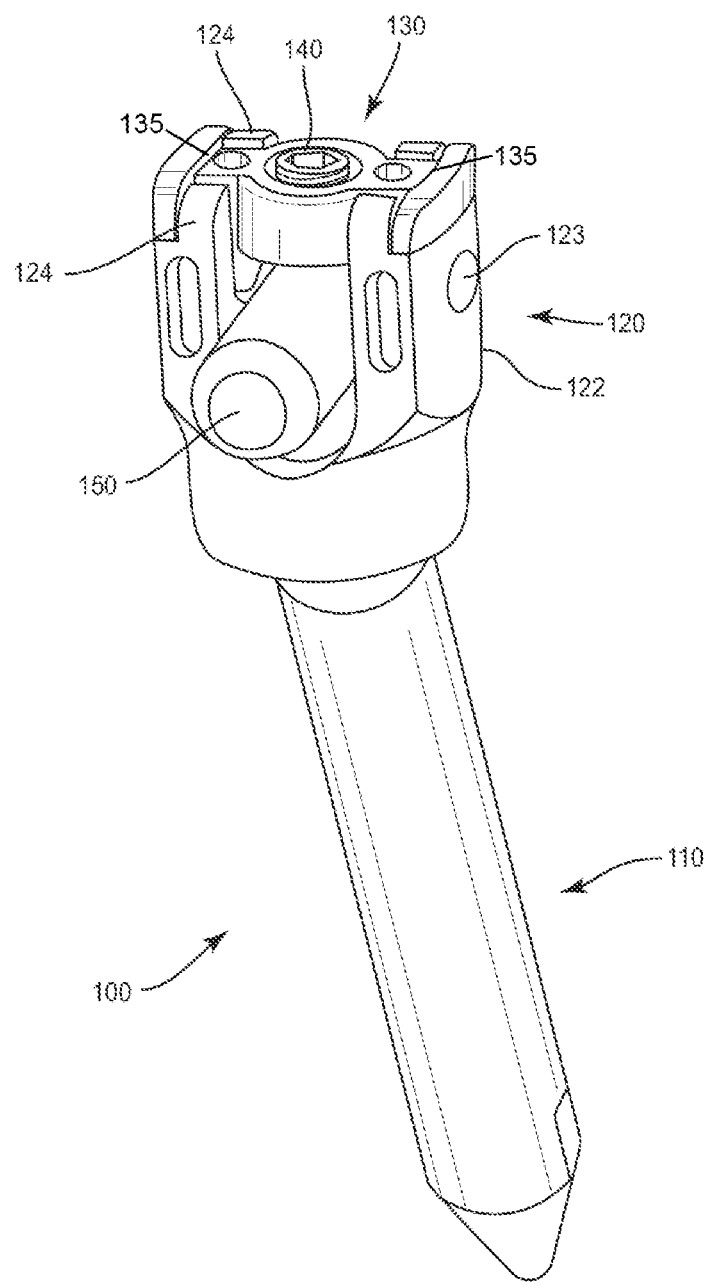
FIG. 5 is a perspective view of the bone fastener system shown in FIG. 1.

Anti-splay member 130 includes a circular portion 131 having an axial aperture 132 defined by an inner threaded surface 138 (FIG. 3). Stems 133 extend radially from the circular portion 131 in opposite directions and each stem 133 terminates in laterally outward extending wings 134 so as to form a retainer with a generally T-shaped arm structure. Each wing 134 has an inner surface 135 (FIGS. 1, 2 and 5) and is configured and dimensioned such that when the anti-splay member 130 is engaged with the receiver 120 as explained below, the inner surfaces 135 of the wings abut the outer surfaces 124a of the teeth (FIGS. 1, 2 and 4) and act as stop surfaces to prevent radial outward movement of the upright arms 122.

The stems 133 each have a cylindrical recess 136 (FIGS. 2, 3 and 4) adapted to receive a tool for insertion of the anti-splay member into the channel 128 formed by the upright arms. The top surface of the anti-splay member 130 is flush with the proximal most surface of the bone fastener 100.

The anti-splay member 130 further includes a pair of opposing resilient arms 137 (FIG. 3) which extend outward and serve as locking members. The arms 137 can possess a barb configuration. The anti-splay member is configured and dimensioned such that the resilient arms 137 bend inwardly to accommodate inertion of the anti-splay member. When insertion is complete and the lateral wings 134 contact upward facing ledge 125, the resilient arms 137 snap outwardly into respective apertures 123 such that the upper edge of each arm 137 abuts the downward facing upper surface 123a of the corresponding aperture 123. This snap-in arrangement prevents disengagement of the anti-splay member from the receiver 120. It is envisioned that member 130 may include one or a plurality of locking members. It is further envisioned that the locking members may be monolithically formed, integrally connected and/or separately attachable with member 130.

The bone fastener 100 is adapted to receive a set screw 140 for securing rod 150 (FIGS. 2, 3 and 4). Set screw 140 is a generally cylindrical member having a threaded outer surface and is adapted to be screwed into threaded axial aperture 132 of the anti-splay member 130. Set screw 140 includes a recess 141 adapted to receive an insertion tool, such as a hex wrench, for applying a torque to the set screw. The set screw is fully inserted when the distal end 143 of the set screw is in contact with the rod 150.

In assembly, operation and use, a vertebral rod system 160 including bone fastener 100 is employed with a surgical procedure for treatment of a spinal disorder affecting a section of a spine of a patient, as discussed herein. The bone fastener 100 may also be employed with other surgical procedures. Bone fastener 100 is employed with a surgical procedure for treatment of a condition or injury of an affected section of the spine including vertebrae V, as shown in FIGS. 6 and 7. It is contemplated that the vertebral rod system 160 including bone fastener 100 is attached to vertebrae V for fusion and/or dynamic stabilization applications of the affected section of the spine to facilitate healing and therapeutic treatment, while providing flexion, extension and/or torsion capability.

In use, to treat the affected section of the spine, a medical practitioner obtains access to a surgical site including vertebrae V in any appropriate manner, such as through incision and retraction of tissues. It is envisioned that the vertebral rod system 160 including bone fastener 100 may be used in any existing surgical method or technique including open surgery, mini-open surgery, minimally invasive surgery and percutaneous surgical implantation, whereby vertebrae V is accessed through a micro-incision, or sleeve that provides a protected passageway to the area. Once access to the surgical site is obtained, the particular surgical procedure is performed for treating the spinal disorder. The vertebral rod system 160 including bone fastener 100 is then employed to augment the surgical treatment. The vertebral rod system 160 including bone fastener 100 can be delivered or implanted as a pre-assembled device or can be assembled in situ. The vertebral rod system may be completely or partially revised, removed or replaced, for example, replacing rod 150 and/or one or all of the components of bone fastener 100.

Vertebral rod 150 has a rigid, rectilinear or optionally arcuate configuration. A first bone fastener 100 is configured to attach an upper section of vertebral rod 150 to vertebra $V_1$. A second bone fastener 100 is configured to attach a lower section of vertebral rod 150 to adjacent vertebra $V_2$. Pilot holes are made in vertebrae $V_1$, $V_2$ for receiving first and second bone fasteners 10. Each bone penetrating member 110 of first and second bone fasteners 100 includes threaded bone engaging shank portion III that are inserted or otherwise connected to vertebrae $V_1$, $V_2$, according to the particular requirements of the surgical treatment. Each retainer 120 of first and second bone fasteners 100 includes channel 124 configured to receive and support rod 150, and a set screw, which is torqued into openings 123 to attach rod 150 in place with vertebrae V, as will be described. It is envisioned that vertebral rod 150 may have a semi-rigid or flexible configuration.

As shown in FIG. 6, the vertebral rod system includes two axially aligned and spaced rods 150, with end sections extending through channels 124 of receivers 120 of the bone fasteners 100. Setscrews 140 through apertures 138 of each anti-splay member 130 are torqued on the end portions of rods 150 to securely attach rods 150 with vertebrae $V_1$, $V_2$. An intervertebral disc $V_3$ is disposed between vertebrae $V_1$ and $V_2$ (FIG. 7). Upon fixation of the vertebral rod system with vertebrae V, bone fasteners 100 each are configured to provide relative pivotable movement, rotation and axial translation of shank 14, as described above, during flexion, extension and/or torsion of the spine.

For example, in an unloaded state of bone fasteners 100 and vertebral rods 150, which corresponds to the first orientation of bone fastener 100 discussed above, there are no appreciable tensile, compressive or torsion loads on vertebrae $V_1$, $V_2$. In flexion, extension and/or torsion of vertebrae V caused by corresponding movement of the patient, bone fasteners 100 react with relative movement of shank 111 to a second, third or more orientation(s).

During movement of vertebrae V, for example, in flexion, extension and/or torsion, shank 111 moves relative to receiver 120 to facilitate relative flexibility and/or movement of rod 150 and/or other components of the vertebral rod system. Shank 111 can pivotally rotate or bend through angle A relative to axis $L_2$ (FIG. 1) and rotate around axes $L_1$ and/or $L_2$ as discussed above. This configuration minimizes stress and facilitates shank 111 movement to avoid failure of bone fastener 100 including, for example, component fracture and/or loosening.

Bone fastener 100 may be employed as a bone screw, pedicle screw or multi-axial screw used in spinal surgery. It is contemplated that bone fastener 100 may be coated with an osteoconductive material such as hydroxyapatite and/or osteoinductive agent such as a bone morphogenic protein for enhanced bony fixation. Bone fastener 100 can be made of radiolucent materials such as polymers. Radiomarkers may be included for identification under x-ray, fluoroscopy, CT or other imaging techniques. Metallic or ceramic radiomarkers, such as tantalum beads, tantalum pins, titanium pins, titanium endcaps and platinum wires can be used, such as being disposed at the end portions of rod 150.

It is envisioned that the vertebral rod system described above including bone fastener 100 may be employed with a vertebral rod having an arcuate configuration and an increased length providing the ability to extend over two or more intervertebral elements. It is contemplated that the configuration of the vertebral rod system may provide load sharing, dynamic and/or flexible stabilization over a plurality of intervertebral levels, including treated and untreated vertebral and intervertebral levels.

In one embodiment, the bone fastener includes an agent, which includes a bone growth promoting material, which may be disposed, packed or layered within, on or about the components and/or surfaces thereof. The bone growth promoting material, such as, for example, bone graft can be a particulate material, which may include an osteoconductive material such as hydroxyapatite and/or an osteoinductive agent such as a bone morphogenic protein (BMP) to enhance bony fixation with the adjacent vertebrae V.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An anti-splay member configured for engagement with a bone fastener, the anti-splay member comprising:

a body defining a longitudinal axis and a threaded cavity extending along the longitudinal axis, the cavity being configured for engagement with a screw, the body having a substantially planar top surface;

opposing retainer members extending substantially perpendicular to the longitudinal axis forming a T-shaped configuration and being configured to engage a proximal end of the bone fastener to prevent radial expansion of the proximal end, the T-shaped configuration is configured for interlocking engagement with a second cavity of the proximal end of the bone fastener, the retainers having surfaces that engage an outer surface of the bone fastener, and a top surface of the retainer members lying flush with a top surface of the bone fastener; and at least one locking member extending from the body and being configured for engagement with the proximal end of the bone fastener.

2. The anti-splay member of claim 1 wherein the retainers have arms spaced from the body.

3. The anti-splay member of claim 1 wherein the body defines at least one surface recess configured for engagement with a surgical instrument that manipulates the fastener.

4. The anti-splay member of claim 1 including a pair of opposing locking members.

5. The anti-splay member of claim 1 wherein the at least one locking member includes an oblique element configured for disposition within a cavity of the proximal end of the bone fastener.

6. The anti-splay member of claim 1 wherein the locking member has a barb configuration.

7. The anti-splay member of claim 1 wherein the body has a low profile configuration such that the body is flush with the proximal most surface of the bone fastener.

8. The anti-splay member of claim 1 wherein the retaining members each define a wing that faces away from the threaded cavity.

9. The anti-splay member of claim 1 wherein the anti-splay member is free of hinges.

10. The anti-splay member of claim 1 wherein the opposing retainer members are symmetrical with respect to one another.

11. A multi-axial bone fastener comprising:

a proximal end including a receiver that defines an implant cavity;

an anti-splay member mounted with the proximal end, the anti-splay member including a body defining a longitudinal axis and a threaded cavity extending along the longitudinal axis, the cavity being configured for engagement with a screw, the body having a substantially planar top surface, the body including opposing retainer members extending substantially perpendicular to the longitudinal axis forming a T-shaped configuration and being configured to engage the proximal end to prevent radial expansion of the proximal end, the T-shaped configuration is configured for interlocking engagement with a cavity of the proximal end, and a top surface of the retainer members lying flush with a top surface of the receiver, the body further including at least one locking member extending therefrom and being configured for engagement with the proximal end; and a distal end configured for penetrating tissue, wherein the receiver includes opposing walls that define the implant cavity, at least one said opposing walls defining an opening for engagement with the locking member.

12. The multi-axial bone fastener of claim 11 wherein the receiver defines a proximal facing cavity configured for engagement with the retainer members.

13. The multi-axial bone fastener of claim 11 wherein the receiver defines a pair of engagement platforms configured for interlocking engagement with the retaining members, each platform including proximal and transverse facing surfaces for engaging the retaining members.

14. The multi-axial bone fastener of claim 11 wherein the body defines at least one surface cavity configured for engagement with a surgical instrument that manipulates the fastener.

15. The multi-axial bone fastener of claim 11 wherein the body includes a pair of opposing locking members.

16. The multi-axial bone fastener of claim 11 wherein the at least one locking member includes an oblique element configured for disposal within a cavity of the proximal end.

17. The multi-axial bone fastener of claim 11 wherein the at least one locking member has a barb configuration.

18. The multi-axial bone fastener of claim 11 wherein the body has a low profile configuration such that the body is flush with a proximal most surface of the receiver.

19. A vertebral rod system comprising;
a multi-axial bone fastener including a proximal end and a distal end, the proximal end of the bone fastener including a receiver having opposing walls that define a U-shaped channel, each of the walls including an engagement platform defining proximal and transverse facing surfaces, and a transverse opening;
an anti-splay member including a body defining a longitudinal axis and a threaded cavity extending along the longitudinal axis, the cavity being configured for engagement with a screw, the body having a substantially planar top surface,
the body including opposing retainer members extending substantially perpendicular to the longitudinal axis forming a T-shaped configuration and being configured to engage the surfaces of the engagement platform to prevent radial expansion of the proximal end, the T-shaped configuration is configured for interlocking engagement with a horizontal upward facing ledge of the proximal end and one of the walls, a top surface of the retainer members lying flush with a top surface of the receiver,
the body further including at least one locking member extending from the body and being configured for engagement with the transverse opening; and
a vertebral rod configured for disposal within the channel.

* * * * *